US00PP28573P3

(12) United States Plant Patent
Holtmaat

(10) Patent No.: US PP28,573 P3
(45) Date of Patent: Oct. 24, 2017

(54) ***ECHINACEA* PLANT NAMED 'RAINB299'**

(50) Latin Name: *Echinacea purpurea*
Varietal Denomination: Rainb299

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 14/756,655

(22) Filed: Sep. 29, 2015

(65) Prior Publication Data

US 2017/0094877 P1 Mar. 30, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

U.S. PATENT DOCUMENTS

| | | | | |
|---|---|---|---|---|
| PP20,687 | P2 * | 1/2010 | van Noor | Plt./428 |
| PP25,523 | P2 * | 5/2015 | Ren | Plt./428 |
| PP26,639 | P3 * | 4/2016 | Ren | Plt./428 |

OTHER PUBLICATIONS

American Nurseryman 2014 Woodies & Perennials 2015 New Plants, retrieved on Dec. 7, 2016, retrieved from the Internet at <http://www.amerinursery-digital.com/dec2014/Default/16/0#&pageSet=3> introductory pp. 1-4 and 30.*

Farwest Portland 2015 New varieties showcase, retrieved on Dec. 7, 2016, retrieved from the Internet at <http://www.farwestshow.com/pdf/nvs15.pdf> ii-xvi (16 pages total).*

* cited by examiner

*Primary Examiner* — June Hwu
(74) *Attorney, Agent, or Firm* — C. A. Whealy

(57) ABSTRACT

A new and distinct cultivar of *Echinacea* plant named 'Rainb299', characterized by its upright and relatively compact plant habit; moderately vigorous to vigorous growth habit; freely branching habit; strong flowering stems; numerous large single-type inflorescences with orange, dark orange, red and red purple-colored ray florets and red-colored receptacle spines; and good garden performance.

2 Drawing Sheets

Botanical designation: *Echinacea purpurea*.
Cultivar denomination: 'RAINB299'.

BACKGROUND OF THE INVENTION

The present invention relates to a new and distinct cultivar of *Echinacea* plant, botanically known as *Echinacea purpurea*, and hereinafter referred to by the name 'Rainb299'.

The new *Echinacea* plant is a product of a planned breeding program conducted by the Inventor in Zuidwolde, The Netherlands. The objective of the breeding program is to develop new freely flowering and relatively compact *Echinacea* plants with unique and attractive ray floret coloration.

The new *Echinacea* plant originated from a cross-pollination in June, 2013 in Zuidwolde, The Netherlands of a proprietary selection of *Echinacea purpurea* identified as code number 304-13, not patented, as the female, or seed, parent with a proprietary selection of *Echinacea purpurea* identified as code number 512-03, not patented, as the male, or pollen, parent. The new *Echinacea* plant was discovered and selected by the Inventor as a single flowering plant from within the progeny of the stated cross-pollination grown in a controlled greenhouse environment in Zuidwolde, The Netherlands in July, 2014.

Asexual reproduction of the new *Echinacea* plant by in vitro meristem culture in a controlled environment in Zuidwolde, The Netherlands since October, 2014 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Rainb299'. These characteristics in combination distinguish 'Rainb299' as a new and distinct *Echinacea* plant:

1. Upright and relatively compact plant habit.
2. Moderately vigorous to vigorous growth habit.
3. Freely branching habit.
4. Strong flowering stems.
5. Numerous large single-type inflorescences with orange, dark orange, red and red purple-colored ray florets and red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are stronger and shorter than plants of the female parent selection.
2. Plants of the new *Echinacea* are not as freely branching as plants of the female parent selection.
3. Plants of the new *Echinacea* and the female parent selection differ in ray floret color as plants of the female parent selection have white-colored ray florets.

Plants of the new *Echinacea* can be compared to plants of the male parent selection. Plants of the new *Echinacea* differ primarily from plants of the male parent selection in the following characteristics:

1. Plants of the new *Echinacea* are stronger and shorter than plants of the male parent selection.
2. Plants of the new *Echinacea* are more freely branching than plants of the male parent selection.
3. Plants of the new *Echinacea* and the male parent selection differ in ray floret color as plants of the male parent selection have pink-colored ray florets.

Plants of the new *Echinacea* can be compared to plants of *Echinacea hybrida* 'Hot Summer', disclosed in U.S. Plant Pat. No. 20,687. In side-by-side comparisons, plants of the new *Echinacea* differed primarily from plants of 'Hot Summer' in the following characteristics:

1. Plants of the new *Echinacea* were shorter than plants of 'Hot Summer'.
2. Plants of the new *Echinacea* are less vigorous than plants of 'Hot Summer'.

Plants of the new *Echinacea* can also be compared to plants of *Echinacea hybrida* 'Cleopatra', disclosed in U.S. Plant Pat. No. 24,631. In side-by-side comparisons conducted in Zuidwolde, The Netherlands, plants of the new *Echinacea* differed primarily from plants of 'Cleopatra' in the following characteristics:

1. Plants of the new *Echinacea* were shorter than plants of 'Cleopatra'.
2. Plants of the new *Echinacea* flowered later than plants of 'Cleopatra'.
3. Plants of the new *Echinacea* and 'Cleopatra' differed in ray floret color as plants of 'Cleopatra' had soft yellow-colored ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Rainb299' grown in ground beds in an outdoor nursery and placed in a 17.5 cm by 22 cm container for the photograph.

The photographs on the second sheet are close-up views of a typical inflorescence (upper photograph) and the upper surface of a typical leaf (lower photograph) of 'Rainb299'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 32° C. and night temperatures ranged from 8° C. to 20° C. Plants were eight months old when the photographs and description were taken. In the following description, color references are made to The Royal Horticultural Society Colour Chart, 2007 Edition, except where general terms of ordinary dictionary significance are used.

Botanical classification: *Echinacea purpurea* 'Rainb299'.

Parentage:

*Female parent*.—Proprietary selection of *Echinacea purpurea* identified as code number 304-13, not patented.

*Male parent*.—Proprietary selection of *Echinacea purpurea* identified as code number 512-03, not patented.

Propagation:

*Type*.—By in vitro meristem culture.

*Time to initiate roots, summer*.—About one week at temperatures about 25° C.

*Time to produce a rooted young plant, summer*.—About five weeks at temperatures about 21° C.

*Root description*.—Fine, fibrous; typically pale cream in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Herbaceous perennial; upright and relatively compact plant habit, narrow inverted triangle; freely branching habit with about four primary branches developing per plant; moderately vigorous to vigorous growth habit.

*Plant height*.—About 68 cm.

*Plant diameter or spread*.—About 54.5 cm.

*Lateral branches*.—Length: About 39.5 cm. Diameter: About 1 cm. Internode length: About 5.1 cm. Aspect: Erect to about 10° from vertical. Strength: Very strong. Texture: Moderately pubescent; strigose; rough. Color: Close to 144B tinged with close to 178B.

Leaf description:

*Arrangement*.—Alternate, simple.

*Length*.—About 20.5 cm.

*Width*.—About 6.6 cm.

*Shape*.—Narrowly ovate.

*Apex*.—Acute.

*Base*.—Attenuate.

*Margin*.—Shallowly dentate; slightly undulate.

*Texture, upper and lower surfaces*.—Moderately pubescent, strigose; rough.

*Luster, upper and lower surfaces*.—Moderately glossy.

*Venation pattern*.—Pinnate.

*Color*.—Developing leaves, upper surface: Close to 143B. Developing leaves, lower surface: Close to 143C. Fully expanded leaves, upper surface: Close to N137A; venation, close to 146D. Fully expanded leaves, lower surface: Close to 147B; venation, close to 145A to 145B and 146D.

*Petioles, basal leaves*.—Length: About 4.1 cm. Diameter: About 3 mm by 4 mm. Strength: Strong, flexible. Texture, upper and lower surfaces: Mostly glabrous; margins, sparsely pubescent; strigose. Color, upper surface: Close to 146D; towards the base, tinged with close to 183B; margins, close to N137A. Color, lower surface: Close to 145B; margins, close to N137C.

Inflorescence description:

*Appearance*.—Large single-type inflorescences with ray and disc florets arranged on a capitulum; inflorescences positioned upright above the foliar plane on mostly upright and strong peduncles.

*Flowering habit*.—Freely flowering habit with about 28 inflorescences developing per plant during the flowering season.

*Fragrance*.—Moderately fragrant; somewhat acidic, pleasant.

*Time to flower*.—In the garden, plants flower continuously from early July to late September in The Netherlands.

*Inflorescence longevity*.—Inflorescences maintain good substance for about three weeks on the plant; inflorescences persistent.

*Inflorescence buds*.—Height: About 2.2 cm. Diameter: About 2.5 cm. Shape: Flattened globular. Color: Involucral bracts, close to 143A; ray florets, close to 150C.

*Inflorescence size*.—Diameter: About 12.9 cm. Depth (height): About 6.7 cm. Disc diameter: About 4 cm. Receptacle height: About 1.6 cm. Receptacle diameter: About 1.3 cm. Receptacle color: Close to 155C.

*Ray florets*.—Quantity and arrangement: About 28 arranged in a single whorl at the base of the receptacle. Length: About 6.1 cm. Width: About 1.4 cm. Shape: Oblanceolate. Apex: Praemorse. Base: Cuneate. Margin: Entire. Texture, upper surface: Glabrous; velvety; longitudinally ridged. Texture, lower surface: Glabrous; longitudinally ridged. Luster, upper surface: Matte. Luster, lower surface: Slightly glossy. Aspect: Horizontal to drooping, about 25° from horizontal. Color: When opening, upper surface: Close to N25A; towards the base, close to 33B. When opening, lower surface: Close to between 51C and 180D; towards the apex, tinged with close to 154D. Fully opened, upper surface: Close to N25B; towards the base, close to 33B and 53D; colors becoming closer to 25D, fading towards the base to closer to 63A to 63B, with development. Fully opened, lower surface: Close to 51B to 51C; towards the apex, tinged with close to 154D; color does not change with development.

*Disc florets*.—Quantity and arrangement: About 250 per inflorescence, spirally at the center. Length: About 1 cm. Diameter: About 2 mm. Shape: Tubular; proximally, 15% free, not fused. Apex: Acute. Base: Fused. Margin: Entire. Texture, inner and outer surfaces: Smooth, glabrous. Luster, inner and outer surfaces: Glossy. Color, when opening, inner and outer surfaces: Apex: Close to 144A tinged with close to 53B. Mid-section: Close to 145C. Base: Close to 59B to 59C. Color, fully opened, inner and outer surfaces: Apex: Close to 144A tinged with close to 53B. Mid-section: Close to 145C. Base: Close to 59B to 59C.

*Receptacle spines*.—Quantity: One per disc floret. Length: About 1 cm to 2 cm. Shape: Acicular. Apex: Acute. Base: Attenuate. Texture: Smooth, glabrous. Luster: Glossy. Color: Apex: Close to 42A to darker than 42A. Mid-section: Close to 143B to 143C. Base: Close to 145D.

*Involucral bracts*.—Quantity per inflorescence: About 96 arranged in about four whorls. Length: About 1.2 cm. Width: About 3 mm. Shape: Ovate to narrowly ovate. Apex: Acute. Base: Cuneate. Margin: Entire. Texture, upper surface: Smooth, glabrous. Texture, lower surface: Moderately pubescent. Luster, upper and lower surfaces: Matte. Color, upper surface: Close to N137B. Color, lower surface: Close to 137A.

*Peduncles*.—Length: About 16.4 cm. Diameter: About 5 mm. Strength: Strong. Aspect: Upright to about 35° from vertical. Texture: Moderately pubescent; strigose. Color: Close to 143C and 144C slightly tinged with close to 178B.

*Reproductive organs*.—Androecium (present on ray and disc florets): Quantity per floret: Five. Filament length: About 3.5 mm. Filament color: Close to 145D. Anther length: About 3 mm. Anther shape: Narrowly oblong. Anther color: Close to 200A. Pollen amount: Moderate. Pollen color: Close to 17A. Gynoecium (present only on disc florets): Quantity per floret: One. Pistil length: About 6 mm. Stigma shape: Decurrent, unequal. Stigma color: Close to 200A. Style length: About 4.5 mm. Style color: Close to 145A. Ovary color: Close to 145D. Seeds and fruits: Seed and fruit development have not been observed on plants of the new *Echinacea*.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Rainb299' as illustrated and described.

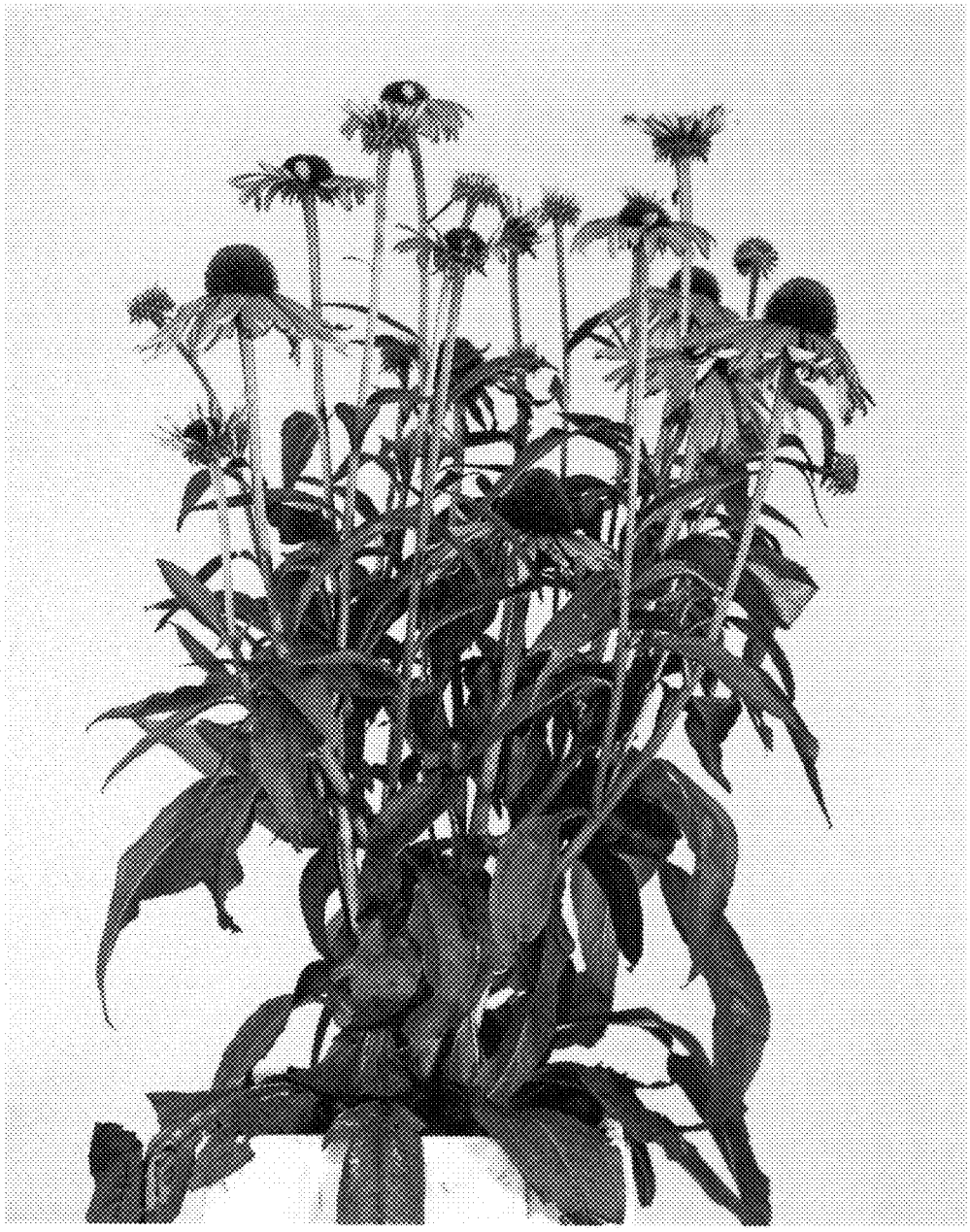

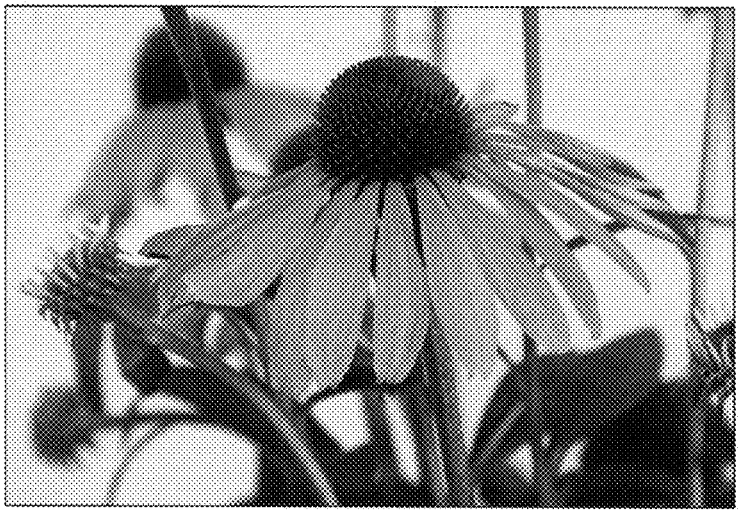
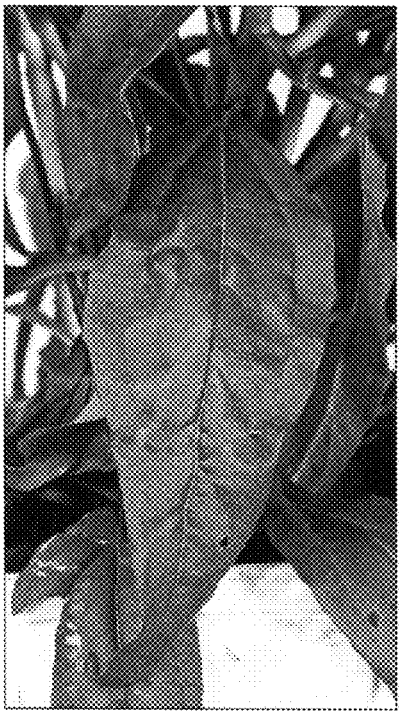

* * * * *